(12) United States Patent
Fischer et al.

(10) Patent No.: US 7,193,091 B2
(45) Date of Patent: Mar. 20, 2007

(54) METHOD FOR THE SIMULTANEOUS PRODUCTION OF TETRAHYDROFURANS AND PYRROLIDONES

(75) Inventors: Rolf-Hartmuth Fischer, Heidelberg (DE); Markus Rösch, Oppenheim (DE); Nils Bottke, Mannheim (DE); Alexander Weck, Freinsheim (DE); Gunther Windecker, Ludwigshafen (DE); Michael Hesse, Worms (DE); Holger Borchert, Offstein (DE); Stephan Schlitter, Limburgerhof (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 394 days.

(21) Appl. No.: 10/505,706

(22) PCT Filed: Feb. 28, 2003

(86) PCT No.: PCT/EP03/02048

§ 371 (c)(1), (2), (4) Date: Aug. 26, 2004

(87) PCT Pub. No.: WO03/074482

PCT Pub. Date: Sep. 12, 2003

(65) Prior Publication Data

US 2005/0119494 A1    Jun. 2, 2005

(30) Foreign Application Priority Data

Mar. 2, 2002    (DE) ................. 102 09 633

(51) Int. Cl.
*C07D 207/267*    (2006.01)
*C07D 307/02*    (2006.01)

(52) U.S. Cl. ............... 548/552; 549/508; 549/325

(58) Field of Classification Search .......... 548/552; 549/476, 475, 507, 508, 325
See application file for complete search history.

(56) References Cited

U.S. PATENT DOCUMENTS

| 5,319,111 A | 6/1994 | Zimmermann et al. |
| 6,008,375 A | 12/1999 | Bergfeld et al. |
| 2003/0106786 A1 | 6/2003 | Kaibel et al. |

FOREIGN PATENT DOCUMENTS

| EP | 443 392 | 8/1991 |
| JP | 2639463 | 8/1997 |
| JP | 2639464 | 8/1997 |
| WO | 93/02068 | 2/1993 |
| WO | 97/24346 | 7/1997 |
| WO | 01/85708 | 11/2001 |

OTHER PUBLICATIONS

Ullmann's Encyclopedia of Industrial Chemistry, 5th Ed., vol. A22, pp. 457-459.

*Primary Examiner*—Joseph K. McKane
*Assistant Examiner*—Rei-tsang Shiao
(74) *Attorney, Agent, or Firm*—Novak Druce & Quigg LLP

(57) ABSTRACT

A process for coproducing alkyl-substituted or unsubstituted THF and pyrrolidones by catalytically hydrogenating C4-dicarboxylic acids and/or derivatives thereof in the gas phase in the presence of copper catalysts and reacting GBL with ammonia or primary amines to give pyrrolidones.

5 Claims, 1 Drawing Sheet

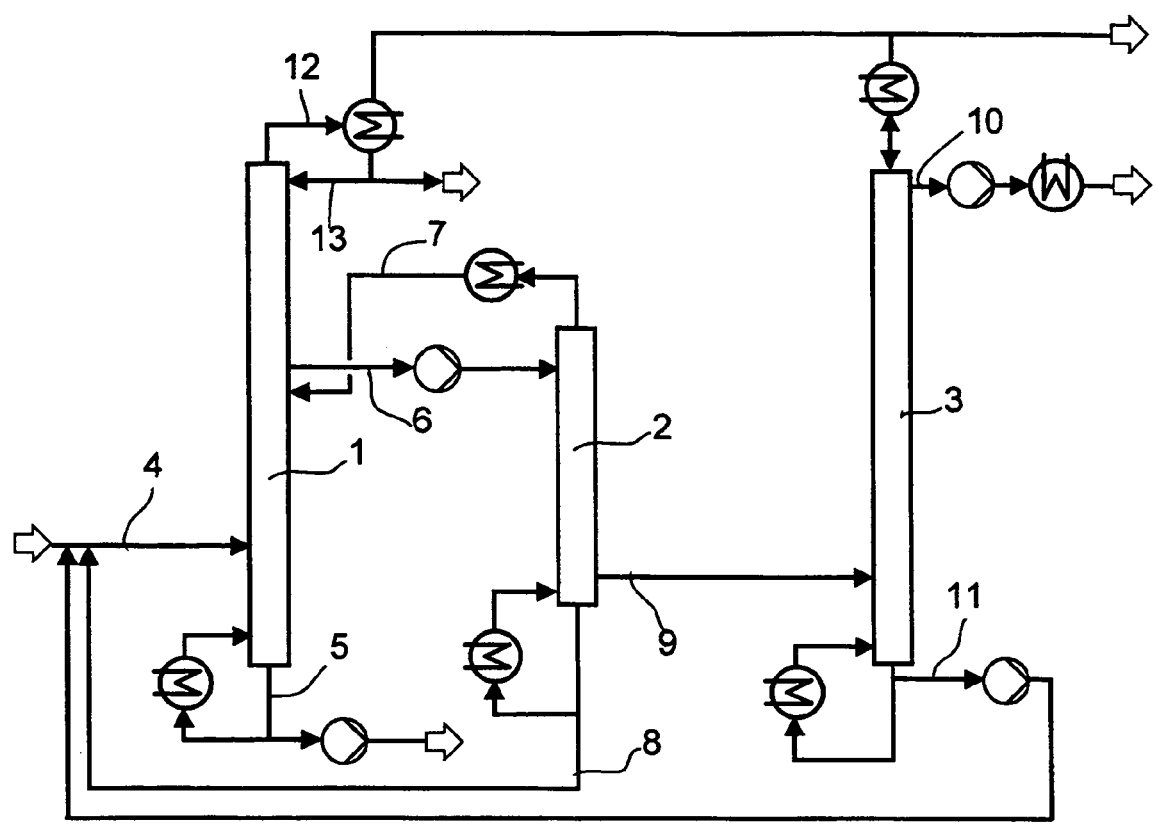

METHOD FOR THE SIMULTANEOUS PRODUCTION OF TETRAHYDROFURANS AND PYRROLIDONES

This application is a 371 of PCT/EP03/02048 filed on Feb. 28, 2003.

The present invention relates to a process for coproducing pure tetrahydrofuran (THF) and pyrrolidones by hydrogenating $C_4$-dicarboxylic acids and/or derivatives thereof, preferably maleic acid and derivatives thereof, in the presence of copper catalysts to give mixtures of THF and gamma-butyrolactone (GBL), distillatively separating said mixtures into THF/water mixtures and GBL-containing mixtures, recovering pure THF and GBL by further distillation and finally reacting GBL with ammonia or primary amines to give pyrrolidone(s).

JP-B 2 639 464 discloses the hydrogenation of maleic anhydride (MA) in the gas phase in the presence of catalysts comprising copper and aluminum oxide to give mixtures of butanediol and tetrahydrofuran. The starting materials used in the hydrogenation in examples 1–4 and 7 are mixtures of MA and GBL. In contrast, example 5 describes the hydrogenation of MA together with dioxane at 210° C./15 bar in the presence of catalysts having copper and aluminum contents of 36.7% and 17.7% respectively to give mixtures comprising 3.8% of butanediol, 81.6% of THF and 14.1% of GBL. Example 6 demonstrates the hydrogenation of MA at 220° C./60 bar in the presence of catalysts having copper and aluminum contents of 28.5% and 24.5% respectively. A disadvantage of the result of example 5 is that in addition to THF and GBL, small but non-negligible quantities of butanediol are also formed, which have to be additionally removed from the THF and GBL products of value and worked up.

JP-B 2 639 463 shows that the gas phase hydrogenation of MA in the presence of catalysts comprising copper, zinc oxide and aluminum oxide likewise gives mixtures of butanediol and THF. Examples 1–6 and 10 also use mixtures of MA and GBL as starting materials. Example 8 describes the hydrogenation of MA together with dioxane at 210° C./15 bar in the presence of catalysts comprising 16% of copper, 35% of zinc and 9.6% of aluminum to give tetrahydrofuran in a yield of 94.1%. Butanediol and GBL were not detected. In contrast, example 9 starting from MA at 220° C./60 bar in the presence of catalysts comprising 18.3% of copper, 36% of zinc and 8.6% of aluminum give hydrogenation yields of 15.3% of butanediol and 83.4% of THF. These results show that the process according to JP 2 639 463 is not suitable for preparing GBL and THF.

WO 97/24 346 describes the gas phase hydrogenation of MA in the presence of catalysts comprising copper, aluminum oxide and binder to give GBL. THF is not detected. For instance, GBL yields of 98.2% are achieved in the presence of a catalyst comprising 84.6% of copper oxide, 9.9% of aluminum oxide and 5.5% of graphite as binder at 275° C. and atmospheric pressure. Over an experimental duration of 1600 hours, the GBL yield was 92–93%. The application further shows that copper catalysts containing chromium oxide deliver low GBL yields and poor catalyst lifetimes. Also, significant quantities of succinic anhydride are formed, which leads to technical problems.

Hydrogenation effluent obtained from WO 97/24 346, example 2 is reacted without workup with methylamine to give N-methylpyrrolidone in example 5. To this end, the water-containing hydrogenation effluent is heated at 290° C. with methylamine. The N-methylpyrrolidone yield determined by gas chromatography was 99.1%. NMP has to be distillatively removed from water, n-butanol and any other by-products in the reaction effluent obtained.

Direct reaction of the hydrogenation effluent with methylamine is disadvantageous for a process producing GBL and THF. It results in possible contamination of the THF formed by nitrogen-containing by-products. High purity requirements are made on fiber grade quality THF, since a large part of the THF is further processed to give polytetrahydrofuran (PolyTHF), the precursor of spandex fibers. The reaction of GBL with ammonia and amines to give pyrrolidones is known per se and described, for example, in Ullmann's Encyclopedia of Industrial Chemistry, 5th revised edition, Volume A 22, pages 457–459.

It is an object of the present invention to provide a process by which pure THF and pyrrolidones are economically coproduced. For this purpose, it is necessary that mixtures of THF and GBL shall initially be produced in desired product ratios and high total yield of THF and GBL by hydrogenating $C_4$-dicarboxylic acids and/or derivatives thereof in the presence of suitable catalysts. These mixtures of THF and GBL shall comprise 5–95 mol % of GBL and 95–5 mol % of THF, preferably 40–90 mol % of GBL and 60–10 mol % of THF, more preferably 65–90 mol % of GBL and 35–10 mol % of THF. In addition, the catalyst shall be compatible with MA which has not undergone complicated purification and, despite this, have a high stability, ie require no frequent regeneration. The mixtures of THF and GBL obtained shall be effectively and economically separable by the process according to the invention, in order to facilitate the preparation of pure THF and pyrrolidones.

We have found that this object is achieved by a process for coproducing alkyl-substituted or unsubstituted THF and pyrrolidones by catalytically hydrogenating $C_4$-dicarboxylic acids and/or derivatives thereof in the gas phase in the presence of copper catalysts and reacting GBL with ammonia or primary amines to give pyrrolidones, which comprises a) hydrogenating $C_4$-dicarboxylic acids and/or derivatives thereof in the gas phase at from 200 to 300° C., from 0.1 to 100 bar, catalyst hourly space velocities of from 0.01 to 1 kg of reactant/l of catalyst*hour and reactant/hydrogen molar ratios of from 20 to 800 in the presence of catalysts comprising copper, aluminum and/or zinc to give mixtures of THF and GBL, b) separating the hydrogenation effluent obtained by distillation into a THF/water mixture as the top product and a GBL-containing bottom product, c) separating the THF/water mixture in a distillation facility consisting of three columns by withdrawing water from the bottom of the first column, recycling water-containing THF from the second into the first column, passing a side stream of the first into the second column, recycling the bottom product of the third column into the first column and withdrawing a distillate at the top of the first column, wherein a side stream of the second column is passed into the third column and the pure THF is obtained as the top product of the third column, d) recovering GBL from the GBL-containing bottom product from step b) by distillation and e) reacting the GBL obtained with ammonia or amines to give corresponding pyrrolidones.

For the purposes of the present invention, $C_4$-dicarboxylic acids and derivatives thereof are maleic acid and succinic acid which may each have one or more $C_1$–$C_6$-alkyl substituents and also the esters and anhydrides of these alkyl-substituted or unsubstituted acids. An example of such an acid is citraconic acid. Preference is given to using the anhydrides of a given acid. Preference is given to maleic acid and/or derivatives thereof. In particular, the reactant used is maleic anhydride (MA). In the process according to the invention, preference is given to using MA which was prepared by oxidizing benzene, $C_4$-olefins or n-butane, extracting the crude MA obtained by oxidation from the crude product mixture using a solvent and then stripping it from the solvent using hydrogen.

The process according to the invention is notable in that it is cost-effective, achieves high THF+GBL total yields of 95% and more, and, by a simple workup, provides on-spec THF and, after reacting GBL with ammonia or amines, on-spec pyrrolidones. The coproduction of THF and pyrrolidones enables the building of larger production plants which are particularly economical owing to economies of scale.

The process may be operated batchwise or continuously, preferably continuously.

According to the invention, the hydrogenation of the $C_4$-dicarboxylic acids and derivatives thereof is carried out in such a way that mixtures of THF and GBL having a GBL content of from 5 to 95 mol %, based on $C_4$-dicarboxylic acids and/or derivatives thereof, preferably from 40–90 mol % and more preferably from 65 to 90 mol % are obtained. The differences between these values and 100% represent the THF contents in each case.

An important aspect of step a) of the process according to the invention is the choice of the catalyst, which has copper oxide as its catalytically active main component. This is applied to an oxidic support which has to have a suitable number of acidic sites. The required quantity of oxidic support depends on the quantity of acidic sites contained therein. A useful support material having a sufficient number of acidic sites is aluminum oxide, whose use is preferred in one embodiment of the present invention. In another embodiment of the present invention, preference is given to using a combination of aluminum oxide with zinc oxide in a weight ratio of from 20:1 to 1:20, preferably from 5:1 to 1:5, as the acidic support material. For materials having a large quantity of such acidic sites, the lower limit of the quantity of the support comprising such material is 20% by weight. The quantity of copper oxide is <80% by weight. Preferred catalyst compositions have <70% by weight of copper oxide and >30% by weight of support, and more preferable catalysts have from 10 to 65% by weight of copper oxide and from 35 to 90% by weight of support.

Low copper oxide contents are preferred because of the resulting cost advantage. The acidic support materials allow high yields to be achieved. The catalysts used according to the invention may contain chromium, but are preferably chromium-free.

The catalysts used may additionally comprise an auxiliary in a quantity of from 0 to 10% by weight. Auxiliaries are organic and inorganic materials which contribute to improved processing during the catalyst preparation and/or to an increase in the mechanical stability of the shaped catalyst. Such auxiliaries are known to those skilled in the art; examples include graphite, stearic acid, silica and copper powder.

The catalysts can be prepared by methods known to those skilled in the art. Preference is given to processes which provide finely divided copper oxide which has been intimately mixed with the other components, and greater preference to precipitation reactions. These involve precipitating precursor compounds dissolved in a solvent in the presence of further metal compounds which are soluble or suspended in the solvent using a precipitant, filtering them off, washing them, drying them and, if desired, calcining them.

These starting materials may be processed by known methods to give shaped articles, for example, by extruding, tableting or agglomeration processes, optionally with the addition of auxiliaries.

Alternatively, catalysts according to the invention may also be prepared, for example, by applying the active component to a support, for example, by impregnation or vapor deposition. Catalysts according to the invention may also be obtained by shaping a heterogeneous mixture of the active component or precursor compound thereof with a support component or precursor compound thereof.

The hydrogenation according to the invention, which, as well as MA, may use other, above-defined $C_4$-dicarboxylic acids or derivatives thereof as reactants, employs the catalyst in reduced, activated form. Activation is effected using reducing gases, preferably hydrogen or hydrogen/inert gas mixtures, either before or after installation into the reactor in which the process according to the invention is carried out.

When the catalyst is installed in the reactor in oxidic form, activation may be carried out either before startup of the plant in which the hydrogenation according to the invention is carried out or else during the startup, ie in situ. Separate activation before startup of the plant is generally effected using reducing gases, preferably hydrogen or hydrogen/inert gas mixtures at elevated temperatures, preferably from 100 to 300° C. In situ activation is effected during running up of the plant by contacting with hydrogen at elevated temperature.

The catalysts are used in the form of shaped articles. Examples include cylindrical extrudates, ribbed extrudates, other extrudate shapes, tablets, rings, spheres and spall.

The BET surface area of the copper catalysts in the oxidic state is from 10 to 400 $m^2/g$, preferably from 15 to 200 $m^2/g$, in particular from 20 to 150 $m^2/g$. The copper surface area ($N_2O$ decomposition) of the reduced catalyst in the installed state is >0.2 $m^2/g$, preferably >1 $m^2/g$, in particular >2 $m^2/g$.

In one variant of the invention, catalysts having a defined porosity are used. These catalysts in the form of shaped articles display a pore volume of $\geq 0.01$ ml/g for pore diameters of >50 nm, preferably of $\geq 0.025$ ml/g for pore diameters of >100 nm and in particular of $\geq 0.05$ ml/g for pore diameters of >200 nm. Additionally, the ratio of macropores having a diameter of >50 nm to the total pore volume for pores having a diameter of >4 nm is >10%, preferably >20%, in particular >30%. The use of these catalysts often enables the achievement of high THF+GBL yields. The porosities reported were determined by mercury intrusion in accordance with DIN 66133. The data were evaluated in the pore diameter range from 4 nm to 300 μm.

The catalysts used according to the invention generally have a sufficient lifetime. However, should the activity and/or selectivity of the catalyst fall in the course of its operating lifetime, they may be restored by measures known to those skilled in the art. Preferably, these include reductive treatment of the catalyst in the hydrogen stream at elevated temperature. The reductive treatment may, if appropriate, be preceded by an oxidative treatment. This involves passing a gas mixture comprising molecular oxygen, for example air, through the catalyst bed at elevated temperature. It is also possible to wash the catalyst with a suitable solvent, for example, ethanol, THF or GBL, and to subsequently dry it in a gas stream.

In order to achieve the THF+GBL yields according to the invention, maintenance of certain reaction parameters is necessary.

An important parameter is the maintenance of a suitable reaction temperature. This is achieved firstly by a sufficiently high entrance temperature of the reactants. This is from >200 to 300° C., preferably from 235 to 280° C. In order to obtain an acceptable, ie high THF+GBL selectivity and yield, the reaction has to be carried out in such a way that the temperature at the catalyst bed, in which the actual reaction takes place, is suitably high.

The hydrogen/reactant molar ratio is likewise a parameter which has an important influence on the product distribution and also the economic viability of the process according to the invention. From an economic point of view, a low hydrogen/reactant ratio is desirable. The lower limit is at a value of about 5, although in general, higher hydrogen/reactant molar ratios of from 20 to 800 are used.

In order to adjust the hydrogen/reactant molar ratios used according to the invention, a portion, advantageously the bulk of the hydrogen is circulated. This is generally effected by a circulation gas compressor known to those skilled in the art. The hydrogen quantity chemically consumed by the hydrogenation is replaced. In a preferred embodiment, a portion of the circulation gas is bled off, in order to remove inert compounds, for example n-butane. The circulated hydrogen may also, if necessary after preheating, be used to vaporize the reactant stream.

The volume stream of the reaction gases, generally expressed as the GHSV (gas hourly space velocity) is also an important quantity for the process according to the invention. The GHSV values of the process according to the invention are from 100 to 10 000 $Nm^3/m^3h$, preferably from 1000 to 3000 $Nm^3/m^3h$, in particular from 1100 to 2500 $Nm^3/m^3h$.

The pressure at which the hydrogenation according to the invention is carried out is from 0.1 to 100 bar, preferably from 2 to 30 bar, in particular from 3 to 20 bar.

In common with the hydrogen circulation gas, all products are circulated which condense out only partially or not at all as the gas stream leaving the hydrogenation reactor cools. These are in particular THF, water and by-products such as methane and butane. The cooling temperature is from 0 to 60° C., preferably from 20 to 45° C. The THF content of the circulation gas is from 0.1 to 5% by volume, in particular from 1 to 3% by volume.

The hydrogenation of MA to THF goes in order through the intermediates succinic anhydride (SA) and GBL. The process according to the invention makes it possible to hydrogenate MA and derivatives thereof to give reaction mixtures comprising 5–95 mol % of THF and correspondingly 95–5 mol % of GBL (based on MA). The GBL/THF ratio can be influenced in particular by the choice of the hyrogenation catalyst, the catalyst hourly space velocity, the hydrogenation temperature, the reaction pressure and the starting product/hydrogen molar ratio. The THF content of the GBL/THF mixtures increases with increasing number of acidic catalyst centers, with decreasing catalyst hourly space velocity, increasing temperature and increasing reaction pressure. A small number of preliminary experiments enables the reaction conditions for the desired GBL/THF molar ratio to be determined.

The literature discloses that THF and GBL are hydrogenated with hydrogen in the presence of copper catalysts to give n-butanol. The process according to the invention is notable for achieving THF+GBL yields of over 90%, sometimes even over 95%, despite the high THF contents in the circulation gas, which are generally easily hydrogenated further to give n-butanol. Useful reactor types include all apparatus which is suitable for heterogeneously catalyzed reactions having a gaseous reactant and product stream. Preference is given to tube reactors, shaft reactors or reactors having internal heat removal means, for example tube bundle reactors, and the use of a fluidized bed is also possible. Greater preference is given to using tube bundle reactors. It is possible to use a plurality of reactors connected in parallel or in series. In principle, streams can be fed in between the catalyst beds. Intermediate cooling between or in the catalyst beds is also possible. When using fixed bed reactors, diluting the catalyst using inert material is possible.

The gas stream leaving the reactor is cooled to from 10 to 60° C. This condenses out to the reaction products which are then passed to a separator. The uncondensed gas stream is withdrawn from the separator and passed to the circulation gas compressor. A small amount of circulation gas is bled off. The condensed reaction products are continuously withdrawn from the system and passed to the work-up. By-products present in the condensed liquid phase are primarily water and n-butanol, as well as small quantities of propanol, methanol, ethanol, n-butyraldehyde, butyl methyl ether and further oxygen-containing compounds.

The process according to the invention is notable in that reactants to be hydrogenated of differing purities may be used in the hydrogenation reaction. It will be appreciated that a reactant of high purity, in particular MA may be used in the hydrogenation reaction. However, the catalyst used according to the invention and the other reaction conditions chosen according to the invention also facilitate the use of reactants, in particular MA, which are contaminated by the customary compounds which occur in the oxidation of benzene, butenes or n-butane and also any other components. Accordingly, the hydrogenation process according to the invention may comprise, in a further embodiment, a preceding step, which comprises the production of the reactant to be hydrogenated by partial oxidation of a suitable hydrocarbon and also the removal of the reactant to be hydrogenated from the resulting product stream.

In particular, the reactant to be hydrogenated is MA. Preference is given to using MA which stems from the partial oxidation of hydrocarbons. Useful hydrocarbon streams include benzene, $C_4$-olefins (e.g. n-butenes, $C_4$-raffinate streams) or n-butane. Greater preference is given to using n-butane, since it is an inexpensive, economical starting material. Processes partially oxidizing n-butane are described, for example, in Ullmann's Encyclopedia of Industrial Chemistry, 6$^{th}$ Edition, Electronic Release, Maleic and Fumaric Acids—Maleic Anhydride.

The reaction effluent obtained is then taken up in a suitable organic solvent or solvent mixture which has a boiling point at atmospheric pressure at least 30° C. higher than that of MA.

This solvent (absorbent) is heated to a temperature in the range from 20 to 160°C., preferably from 30 to 80° C. The gas stream comprising maleic anhydride from the partial oxidation may be brought into contact with the solvent in various ways: (i) passing the gas stream into the solvent (for example, via gas introduction nozzles or sparging rings), (ii) spraying the solvent into the gas stream, and (iii) counter-current contact between the gas stream flowing upward and solvent flowing downward in a column provided with trays or packing. In all three variants, the apparatus known to those skilled in the art for gas absorption may be used. When choosing the solvent to be used, care has to be taken to ensure that it does not react with the starting material, for example the MA which is preferably used. Useful solvents include: tricresyl phosphate, dibutyl maleate, high molecular weight waxes, aromatic hydrocarbons having a molecular weight of from 150 to 400 and a boiling point above 140° C., such as dibenzylbenzene; dialkyl phthalates having $C_1$–$C_8$- alkyl groups, for example, dimethyl phthalate, diethyl phthalate, dibutyl phthalate, di-n-propyl phthalate and di-isopropyl phthalate; di-$C_1$–$C_4$-alkylesters of other aromatic, aliphatic and cycloaliphatic dicarboxylic acids, for example dimethyl-2,3-naphthalenedicarboxylic acid, dimethyl-1,4-cyclohexanedicarboxylic acid, methylesters of long-chain fatty acids having, for example, from 14 to 30 carbon atoms; high-boiling ethers, for example dimethyl ethers of polyethylene glycol, for example tetraethylene glycol dimethyl ether.

The solution resulting from treatment with the absorbent generally has an MA content of from about 5 to 400 grams per liter.

The offgas stream remaining after treatment with the absorbent primarily comprises the by-products of the preceding partial oxidation, such as water, carbon monoxide, carbon dioxide, unconverted butanes, acetic acid and acrylic acid. The offgas stream is virtually free of MA.

The dissolved MA is subsequently stripped from the absorbent. In the stripping column, a temperature profile is observed which is determined by the boiling points of MA at the top of the column and the virtually MA-free absorbent at the bottom of the column at the prevailing column pressure and the chosen carrier gas dilution.

In order to prevent solvent losses, rectification internals may be disposed above the feed point of the crude MA stream. The virtually MA-free absorbent withdrawn at the bottom is returned to the absorption zone. In the case of direct stripping using hydrogen, a virtually saturated gas stream of MA in hydrogen is withdrawn at the top of the column. Otherwise, the condensed MA is pumped into a vaporizer and vaporized there into the circulation gas stream.

The MA/hydrogen stream further comprises by-products formed in the partial oxidation of n-butane, butenes or benzene using oxygen-containing gases, and also absorbent which has not been removed. These include the by-produced acetic acid and acrylic acid, water, maleic acid and also the compounds used as absorbents. The MA contains acetic acid in quantities of from 0.01 to 1% by weight, preferably from 0.1 to 0.8% by weight and acrylic acid in quantities of from 0.01 to 1% by weight, preferably from 0.1 to 0.8% by weight, based on MA. In the hydrogenating step, some or all of the acetic acid and acrylic acid are hydrogenated to give ethanol and propanol respectively.

The maleic acid content is from 0.01 to 1% by weight, in particular from 0.05 to 0.3% by weight, based on MA.

When dialkyl phthalates are used as absorbents, their content in MA depends strongly on correct operation at the stripping column, in particular the enrichment section. Phthalate contents of 1.0% by weight, in particular of 0.5% by weight, should not be exceeded under appropriate operation, since too much absorbent is otherwise consumed.

The hydrogen/maleic anhydride stream obtained in this way is then passed to the hydrogenation zone and hydrogenated as described above. The catalyst activity and lifetime are virtually unchanged compared with the use of extensively prepurified, for example by distillation, MA. The process according to the invention enables THF+GBL yields of about 90%, in favorable cases about 95%. A high product selectivity is also achieved.

The condensed hydrogenation effluent is distillatively separated in step b) into a THF/water mixture as top product and a GBL-containing bottom product. This is effected in a distillation column at a pressure of 1.3 bar absolute, top temperatures of from 70 to 80° C. and bottom temperatures of from 200 to 220° C.

The recovery of pure THF by distillation in three columns is disclosed by DE 3 726 805. In the first two columns, the THF/water azeotrope is broken by two-pressure distillation, and the THF is purified by distillation in the third column. The bottom product of the first column comprises, in addition to by-products which are high-boiling compared to THF, all of the remaining GBL. However, the water-containing crude THF products, in particular the THF/water azeotropes, from the gas phase hydrogenation of MA are not sufficiently purified by the process disclosed by DE 37 26 805 to fulfill the THF purity requirements relating in particular to the further processing of THF, for example to give PTHF.

In a novel process which is the subject matter of a commonly assigned parallel German application having the title "Distillative workup of THF", the distillation of the crude water-containing THF/water azeotrope in step c) of the process according to the invention is carried out in three columns connected in series as shown in the figure. The columns are operated in a manner known per se, and the first column (1) is operated with a pressure of 1.3 bar with at least 10, preferably from 30 to 70, more preferably from 45 to 55, theoretical plates and a reflux ratio, based on the sidestream (6) of from 0.5 to 5, the second column (2) with at least 10, preferably from 30 to 70, more preferably from 45 to 55, theoretical plates, a pressure of from 5 to 10 bar, preferably from 7 to 9 bar, more preferably 8 bar, and the third column (3) with at least 10 theoretical plates, preferably from 30 to 70 plates, more preferably from 45 to 55 theoretical plates, at a pressure of from 0.9 to 2 bar, preferably from 1 to 1.5 bar and more preferably 1.3 bar and a reflux ratio of about 3.8.

Each of the three columns (1), (2) and (3) has at least one theoretical plate, which is characterized by the vapor stream formed and the liquid reflux of the plate being fed past each other in countercurrent. The internal fitments of the columns (1), (2) and (3) may comprise dumped packings, fabric packings or sheet metal packings, or trays such as valve trays, tunnel-cap trays or sieve trays. A definition of a theoretical plate may be found, for example, in E.-U. Schlunder, F. Thurner, Destillation, Absorption, Extraktion, Thieme Verlag 1986, page 66 and pages 131–132.

The crude THF/water mixture from step b) which was obtained according to a) by gas phase hydrogenation of MA and subsequent removal of the GBL according to b), generally consists of varying quantities of THF as the main product, from 10 to 20% by weight of n-butanol (n-BuOH), from 0.1 to 1% by weight of methanol (MeOH), ethanol (EtOH) and propanol (ProOH), from 100 to 500 ppm of gamma-butyrolactone (GBL), about 100 ppm of butyraldehyde (BA) and butyl methyl ether (BME), further oxygen-functionalized CH compounds in concentrations of <200 ppm, and also water.

Introduction into the first column is effected at the side through the inlet (4). The inlet (4) is conveniently disposed in the lower half above the bottom of the column. According to the invention, it has been found that the feed should be disposed between the 1st and 30th theoretical plate, preferably between the 1st and 20th theoretical plate, most preferably between the 1st and 10th theoretical plate. Water and high-boiling components which have a higher boiling point than THF, such as gamma-butyrolactone, ethanol, propanol and butanol are discharged (5) together with water from the bottom of the column. The low-boilers which have a higher boiling point than THF, such as methanol, are withdrawn overhead via line (12) with THF, partially condensed by a heat exchanger and passed as reflux (13) back into column (1). The column (1) has, disposed above the inlet (4), a sidestream takeoff (6), through which a preferably liquid THF/water mixture (which may, however, be gaseous or a liquid/gas mixture) is withdrawn and introduced with increasing pressure via a pump into the side of the intermediate pressure column (2).

The sidestream takeoff (6) is disposed between the 20th and 70th theoretical plate of the column (1), preferably between the 30th and 55th plate, more preferably between the 30th and 40th plate.

In the sidestream (6), THF is present in a weight ratio to water of from 13:1 to 25:1, preferably in a ratio of from 15:1 to 22:1.

The sidestream mixture (6) is fed into the upper section of the intermediate pressure column (2), between the 30th and 70th theoretical plate, preferably between the 40th and 60th plate, more preferably between the 50th and 60th plate. By shifting the azeotropic point of the THF/water mixture, the mixture is separated again in the intermediate pressure column (2). From the head of this intermediate pressure column, water-rich THF is condensed by a heat exchanger and recycled (7) into the first column between the sidestream takeoff (6) and the column bottom. The bottom product of this intermediate pressure column (2) which is substantially water-free and consists of THF and high-boilers, for example, butyraldehyde, butyl methyl ether and further high-boiling oxygen-functionalized CH compounds, is recycled via line (8) and may be mixed with crude water-containing THF, and reintroduced as feed into column (1) via line (4).

In the stripping section of the intermediate pressure column (2), THF accumulates to over 99% by weight. In order to avoid entraining the steam-volatile components into the column (3), a preferably liquid THF-rich stream, which may, however, also be gaseous or a liquid/gas mixture, is withdrawn between the vapor phase of the bottom and half of the number of theoretical plates in the column as a liquid sidestream (9) just above the base of the intermediate pressure column (2).

The sidestream (9) withdrawn from the column (2) comprises from 50 to 100% by weight of THF, preferably from 80 to 100% by weight, more preferably from 95 to 100% by weight of THF.

The sidestream (9) is fed into column (3) above the bottom. The feed point is between the 1st and 30th theoretical plate, preferably between the 1st and 15th plate, more preferably between the 5th and 10th plate. Pure THF is withdrawn at the top of the column (10) in liquid or gaseous form or as a liquid/gas mixture, preferably liquid, while the liquid bottom product (11) is recycled into column (1) by a pump. The pure THF obtained is suitable in particular for further processing to give PolyTHF and spandex fibers.

The GBL-containing bottom product from step b) is a mixture of water, n-butanol and GBL and may be reacted in a manner known per se in the presence or absence of catalysts directly, ie without further workup, with ammonia or amines to give pyrrolidones which may in turn be distillatively purified. However, preference is given to first distillatively purifying the GBL-containing bottom product. GBL may be reacted with ammonia and amines, for example, by the processes described in WO 97/24346 or DE 1 795 007 or according to the German application DE 10156885.1.

The process according to the present invention is illustrated by the examples which follow.

EXAMPLES a) Catalyst Preparation (Catalyst C)

A heatable precipitation vessel equipped with a stirrer is initially charged with 1.5 l of water and heated to 80° C. Over the course of an hour, a metal salt solution comprising 731 g of $Cu(NO_3)_2 \cdot 2.5 H_2O$ and 1840 g of $Al(NO_3)_3 \cdot 9 H_2O$ in 2000 ml of water and 20% by weight sodium carbonate solution are simultaneously metered into this precipitation vessel with stirring until a pH of 8 is achieved in the precipitation vessel and the stirring is continued for a further 15 min at this pH. A total of 5.6 kg of sodium carbonate solution is used. The suspension formed is filtered off and washed with water until the washings contain no more nitrate (<25 ppm). The filtercake is first dried at 120° C. and then calcined at 600° C. The catalyst prepared in this way contains 50% by weight of CuO and 50% by weight of $Al_2O_3$. 400 g of this catalyst powder are comminuted to a particle size of <1 mm, and mixed with 12 g of graphite powder, intimately mixed and compressed to give tablets of 3 mm diameter and 3 mm thickness.

The catalysts A and B were similarly prepared using zinc nitrate:

Catalyst A: 70% by weight of CuO, 25% by weight of ZnO, 5% by weight of $Al_2O_3$ Catalyst B: 40% by weight of CuO, 40% by weight of ZnO, 20% by weight of $Al_2O_3$ b) Activation of the Catalysts A to C Before the start of the reaction, the catalyst is subjected to a hydrogen treatment in the hydrogenation apparatus.

The hydrogenation reactor of the hydrogenation apparatus is filled with different quantities of catalyst and purged with 500 l/h (stp) of $N_2$ at atmospheric pressure. The catalyst bed is then heated to the temperature given in table 1 and treated for different times with mixtures of hydrogen and nitrogen. Sequences, reduction times, temperature and mixing ratios are given in the following table 1.

TABLE 1

| Catalyst | Time [min] | Temperature [° C.] | $N_2/H_2$ mixtures | |
|---|---|---|---|---|
| | | | $N_2$ [l/h, stp] | $H_2$ [l/h, stp] |
| A, C | 70 | 250 | 500 | 10 |
| | 30 | | 300 | 10 |
| | 720 | | 0 | 60 |
| B | 40 | 160 | 300 | 25 |
| | 20 | | 100 | 25 |
| | 20 | | 0 | 25 |
| | 720 | | 0 | 65 | c) Hydrogenation Apparatus

The pressure apparatus used for the hydrogenation comprises a vaporizer, a reactor, a condenser having a quench feed, a hydrogen inlet, an offgas line and a circulation gas blower. The pressure in the apparatus is kept constant.

The molten MA is pumped in cocurrent with hydrogen into the preheated (245° C.) vaporizer and vaporized. A mixture of fresh hydrogen and circulation gas likewise flows through the vaporizer from the top. Hydrogen and MA thus flow from the bottom into the heated reactor. The reactor contents comprise a mixture of glass rings and catalyst. After the hydrogenation, the reaction products formed together with hydrogen leave the reactor and are condensed in a condenser. A portion of the circulation gas is bled off before the remainder, mixed with fresh hydrogen, flows back into the vaporizer.

The condensed liquid reaction effluent, the offgas and the circulation gas are quantitatively analyzed by gas chromatography.

d) Hydrogenation of Maleic Anhydride Prepared from n-butane

Example 1

The reactor of the hydrogenation apparatus described in 1c is filled with 220 ml of catalyst A (prepared in analogy to catalyst C) and 126 ml of Raschig rings. Activation was effected as described in 1b.

The reactant used was maleic anhydride prepared from n-butane which comprised 500 ppm of acrylic acid, 1500 ppm of acetic acid and 100 ppm of dibutyl phthalate. The reaction is carried out for 1000 h. Over the total duration, no deactivation of the catalyst is observed, ie no reduction of the maleic anhydride conversion and/or the GBL and tetrahydrofuran yields. Table 2 summarizes the reaction parameters of the hydrogenation and the results.

Example 2 a) and 2 b)

Catalyst B (prepared in analogy to catalyst C), which comprises 40% of copper oxide, 40% of zinc oxide and 20% of aluminum oxide, is installed in the above-described hydrogenation apparatus and pretreated with hydrogen as described in 1b. The contents of the reactor comprised 220 ml of catalyst B and 126 ml of Raschig rings. The reactant used was pure maleic anhydride prepared from n-butane. The reaction parameters and results are presented in table 2.

Example 3

The reactor of the hydrogenation apparatus described in 1c was filled with a mixture of 80 ml of catalyst C and 80 ml of Raschig rings. The remaining volume was filled with Raschig rings. Activation was effected as described in 1b. The reactant used was maleic anhydride prepared from n-butane which comprised 1000 ppm of acrylic acid, 1500 ppm of acetic acid and 100 ppm of dibutyl phthalate. The reaction was carried out for 1000 h. Over the total duration, no deactivation of the catalyst was observed, ie no reduction of the maleic anhydride conversion and/or the GBL and tetrahydrofuran yields. Table 2 summarizes the reaction parameters of the hydrogenation and the results.

Example 4 a) Separation of THF and GBL

The hydrogenation effluent from example 2a) having the composition reported in table 2 was distillatively separated according to the invention into a THF/water mixture and GBL in a column having 15 theoretical plates at 1.3 bar absolute, a bottom temperature of 214° C. and a top temperature of 76° C. The feed stream comprising the hydrogenation effluent was separated in the mass ratio bottom product:top product of 70:30.

b) Purification of THF

The distillation apparatus shown in the figure was used. It consists of three columns (1), (2) and (3), of which column (1) has 48 and column (3) has 45 theoretical plates and both are operated at 1.3 bar absolute. Column (2), which is operated at elevated pressure of 8 bar, has 43 theoretical plates.

The top product of the THF/GBL column, a water-containing THF mixture comprising 77.2% by weight of THF, 18.4% by weight of n-BuOH, 0.3% by weight of MeOH, 0.5% by weight of EtOH, 0.5% by weight of PrOH, 134 ppm of GBL, 110 ppm of BA and 90 ppm of BME was introduced into column (1) via the inlet (4). The remainder comprises further O-functionalized CH compounds and largely water.

Simultaneously, column (1) was fed with the bottom stream of column (2) via inlet (8) and with the bottom stream of column (3) via line (11). Column (1) was operated with a sidestream takeoff (6), a top takeoff (12) and a bottom takeoff (5). The reflux ratio based on the sidestream was 1.1. The bottom takeoff (5) drew off water and high-boilers. The sidestream (6) withdrawn from column (1) was water-containing THF having a water content of 4.2% by weight and a THF concentration of 83% by weight. The top takeoff (12) withdrew a little more than 0.05% of the feed. The top stream had a THF concentration of 66% by weight and a methanol content of 30% by weight. The sidestream (6) of the first column was fed with increasing pressure into the second column (2) which was operated at 8 bar. The top stream (7) of the second column which contained virtually all the water and the bulk of the narrow-boiling components was recycled into the first column (1). A strongly THF-enriched stream is withdrawn as a liquid sidestream (9) just above the base and passed on into column (3). The bottom stream of column (2) which was found to be virtually water-free was recycled via line (8). Ultrapure THF was withdrawn overhead (10) from the third column (3), while the bottom product was recycled into column (1) by a pump.

The purity of the THF prepared in this way was 99.97% by weight. The quantities of each of the by-products n-butyraldehyde and n-butyl methyl ether were only 0.001% by weight.

TABLE 2

| Ex. | Cat. | Temp. [° C.] | Pressure [bar] | Catalyst hourly space velocity [$kg_{MA}/Kg_{cat}h$] | $H_2$/MA [mol/mol] | Conversion [%] | GBL [%] | Butanol [%] | BDO[1] [%] | THF [%] | SA[2] [%] | THF[3] [%] |
|---|---|---|---|---|---|---|---|---|---|---|---|---|
| 1 | A | 240 | 15.3 | 0.1 | 75 | 100 | 38.5 | 3.1 | 0 | 50.5 | 0.2 | 56 |
| 2a | B | 250 | 10 | 0.24 | 90 | 100 | 66.7 | 4.8 | 3 | 20.7 | 0.13 | 23 |
| 2b |   | 250 | 2 | 0.11 | 76 | 100 | 83.4 | 4.9 | 0.5 | 7 | 1.1 | 7 |
| 3 | C | 257 | 5 | 0.11 | 95 | 100 | 9.9 | 5.7 | 0 | 83.2 | 0.1 | 89 |

[1] Butanediol
[2] Succinic anhydride
[3] Based on the sum of GBL and THF

Example 5

Crude GBL obtained from example 4.1 was reacted without further purification with methylamine at 290° C. according to WO 97/24 346, example 5. The N-methylpyrrolidone yield determined by gas chromatography was 98.5% (based on GBL used).

We claim:

1. A process for coproducing alkyl-substituted or unsubstituted THF and pyrrolidones by catalytically hydrogenating $C_4$-dicarboxylic acids and/or derivatives thereof in the gas phase in the presence of copper catalysts and reacting GBL with ammonia or primary amines to give pyrrolidones, which comprises
    a) hydrogenating $C_4$-dicarboxylic acids and/or derivatives thereof in the gas phase at from 200 to 300° C., from 0.1 to 100 bar, catalyst hourly space velocities of from 0.01 to 1 kg of reactant/ of catalyst*hour and reactant/hydrogen molar ratios of from 20 to 800 in the presence of supported catalysts comprising 70% by weight of copper oxide and >30% by weight of support material selected from aluminum oxide or aluminum oxide and zinc oxide to give mixtures of THF and GBL,
    b) separating the hydrogenation effluent obtained by distillation into a THF/water mixture as the top product and a GBL-containing bottom product,
    c) separating the THF/water mixture from step b) in a distillation facility consisting of three columns by withdrawing water from the bottom of the first column, recycling water-containing THF from the second into the first column, passing a side stream of the first into the second column, recycling the bottom product of the third column into the first column and withdrawing a distillate at the top of the first column, wherein a side stream of the second column is passed into the third column and the pure THF is obtained as the top product of the third column,
    d) recovering GBL from the GBL-containing bottom product from step b) by distillation and
    e) reacting the GBL obtained with ammonia or amines to give corresponding pyrrolidones.

2. A process as claimed in claim 1, wherein the reactant used in the reaction is maleic anhydride.

3. A process as claimed in claim 1, wherein the process is operated over a catalyst comprising <70% by weight of CuO and >30% by weight of an oxidic support having acidic sites and at catalyst hourly space velocities of from 0.01 to 1.0 kg of reactants of catalyst*hour.

4. A process as claimed in claim 1, wherein the oxidic support is $Al_2O_3$ or $Al_2O_3/ZnO$ in a weight ratio of from 20:1 to 1:20.

5. A process as claimed in claim 1, wherein the GBL-containing bottom product obtained in step b) is reacted directly in the presence or absence of catalysts with ammonia or amines to give corresponding pyrrolidones.

* * * * *

UNITED STATES PATENT AND TRADEMARK OFFICE
CERTIFICATE OF CORRECTION

PATENT NO. : 7,193,091 B2 Page 1 of 1
APPLICATION NO. : 10/505706
DATED : March 20, 2007
INVENTOR(S) : Fischer et al.

It is certified that error appears in the above-identified patent and that said Letters Patent is hereby corrected as shown below:

Claim 1, column 13, line 18: "reactant/ of" should read --reactant/1 of--

Claim 3, column 14, line 20: "reactants" should read --reactant/1--

Signed and Sealed this

First Day of May, 2007

JON W. DUDAS
*Director of the United States Patent and Trademark Office*